United States Patent
Kinugawa et al.

(10) Patent No.: US 7,048,891 B2
(45) Date of Patent: May 23, 2006

(54) CATALYST DETERIORATION DETECTING APPARATUS

(75) Inventors: Masumi Kinugawa, Okazaki (JP); Kiyonori Sekiguchi, Okazaki (JP); Tsukasa Kuboshima, Okazaki (JP)

(73) Assignee: Denso Corporation, (JP)

(*) Notice: Subject to any disclaimer, the term of this patent is extended or adjusted under 35 U.S.C. 154(b) by 579 days.

(21) Appl. No.: 10/176,638

(22) Filed: Jun. 24, 2002

(65) Prior Publication Data

US 2002/0197721 A1    Dec. 26, 2002

(30) Foreign Application Priority Data

Jun. 22, 2001   (JP)   ............... 2001-189165
Jun. 5, 2002    (JP)   ............... 2002-163974

(51) Int. Cl.
*G01N 31/12*   (2006.01)
*G05D 23/00*   (2006.01)
*F01N 3/18*    (2006.01)
*G01N 31/10*   (2006.01)

(52) U.S. Cl. ............... 422/94; 60/277; 60/285; 60/299; 422/83; 422/95; 422/98; 422/108; 422/109; 436/37; 436/137; 436/155; 436/159

(58) Field of Classification Search ............... 60/274, 60/277, 285, 299; 422/83, 94–95, 108–109, 422/98; 436/37, 137, 155, 159

See application file for complete search history.

(56) References Cited

U.S. PATENT DOCUMENTS

| | | | | |
|---|---|---|---|---|
| 3,882,451 | A | * | 5/1975 | Fujishiro et al. ............ 340/449 |
| 4,953,351 | A | * | 9/1990 | Motz et al. ............ 60/285 |
| 5,133,184 | A | * | 7/1992 | Geiger ............ 60/274 |
| 5,339,628 | A | * | 8/1994 | Maus et al. ............ 60/277 |
| 5,419,122 | A | * | 5/1995 | Tabe et al. ............ 60/274 |
| 5,444,974 | A | * | 8/1995 | Beck et al. ............ 60/274 |
| 5,706,652 | A | * | 1/1998 | Sultan ............ 60/274 |
| 5,842,341 | A | * | 12/1998 | Kibe ............ 60/274 |
| 5,851,376 | A | * | 12/1998 | Nishioka et al. ......... 205/784.5 |
| 5,854,079 | A | | 12/1998 | Kato |
| 6,145,302 | A | * | 11/2000 | Zhang et al. ............ 60/274 |
| 6,167,698 | B1 | * | 1/2001 | King et al. ............ 60/286 |
| 6,276,128 | B1 | * | 8/2001 | Kammann et al. ............ 60/274 |

FOREIGN PATENT DOCUMENTS

| | | |
|---|---|---|
| EP | 0 779 416 A1 | 6/1997 |
| JP | 3-50315 | 3/1991 |
| JP | 7-180536 | 7/1995 |
| JP | 2593506 | 12/1996 |
| JP | 9-166015 | 6/1997 |

* cited by examiner

*Primary Examiner*—Arlen Soderquist
(74) *Attorney, Agent, or Firm*—Nixon & Vanderhye PC

(57) ABSTRACT

A heat generation amount qr/r per unit flow amount of combustible substances supplied to a catalyst is estimated based on upstream and downstream temperature information and supplemental engine information. A deteriorated condition of the catalyst is detected based on a judgement whether or not the estimated heat generation amount is smaller than a predetermined judging value D.

9 Claims, 10 Drawing Sheets

CATALYST DETERIORATION DETECTING APPARATUS

BACKGROUND OF THE INVENTION

The present invention relates to an exhaust gas purification system which purifies harmful substances contained in exhaust gas of an engine, and more particularly to a catalyst deterioration detecting apparatus for accurately detecting a deteriorated condition of a catalyst used for oxidizing combustible substances (e.g., HC) contained in the exhaust gas of a diesel engine. The present invention also relates to a catalyst deterioration alarming apparatus for alarming the deterioration of the catalyst.

The gasoline engine is generally equipped with an oxygen concentration sensor to detect the oxygen concentration in the exhaust gas and to control an air-fuel ratio of gas mixture introduced into a combustion chamber of this engine. It is conventionally known that the oxygen concentration sensor can be used to detect deterioration of a ternary catalyst.

Diesel engines are characterized in that the air-fuel ratio is set to a lean region compared with a theoretical air-fuel ratio. The catalyst deterioration judging method employed for gasoline engines cannot be directly applied to the diesel engines.

It may be useful to use a hydrocarbon (HC) sensor to judge the deterioration of a catalyst. However, a reliable HC sensor has not been developed yet. And also, the HC sensor will be expensive.

Japanese patent No. 2593506 discloses a conventional method for judging the deteriorated condition of a catalyst based on a difference between an upstream exhaust gas temperature and a downstream exhaust gas temperature of a catalytic converter. This judging method is non-expensive because the exhaust gas temperature sensor equipped in a catalyst container can be utilized for this judgement. However, this judging method has not been practically used because the detection accuracy is not yet assured for every operating mode of an engine and also because the measuring accuracy of each exhaust gas temperature sensor is not yet reliable.

Unexamined Japanese patent publication No. 3-50315 discloses a technique for optimizing the detecting point for improving the detecting accuracy of the exhaust gas temperature in a catalytic converter.

Unexamined Japanese patent publication No. 7-180536 discloses a technique for mutually correcting the temperature data obtained from two exhaust gas temperature sensors considering specific conditions.

However, these conventional techniques are insufficient for solving the above-described deficiencies of Japanese patent No. 2593506.

FIG. 11 is a graph showing a relationship between HC flow amount per unit time (g/hr) and upstream/downstream exhaust gas temperature difference (° C.) in relation to catalytic purification rate (η), obtained experimentally through engine tests performed in an emission mode operating region according to which the concentration of combustible substances (HC) flowing into a catalytic converter and the catalytic purification rate (η) are changed variously.

In these tests, measurement of an upstream exhaust gas temperature and a downstream exhaust gas temperature was done accurately. The measuring error of each exhaust gas temperature sensor is negligible.

As understood from FIG. 11, it is difficult to accurately judge the deteriorated condition of a catalyst based on only the upstream/downstream exhaust gas temperature difference.

Furthermore, in the case of diesel engines, a diesel particulate filter (referred to as DPF) is used to trap the exhaust gas emissions called particulates. When a direct-type diesel engine is equipped with a DPF carrying a catalyst oxidizing the combustible substances (HC), it is difficult to directly measure the catalyst temperature in this DPF. It is, hence, necessary to detect the deterioration of the catalyst based on the difference of upstream and downstream exhaust gas temperatures of DPF. Considering such circumstances, it is earnestly requested to provide a high-accurate and non-expensive catalyst deterioration detecting apparatus.

SUMMARY OF THE INVENTION

In view of the above-described problems of conventional techniques, the present invention has an object to provide a catalyst deterioration detecting apparatus which is capable of accurately detecting the deteriorated condition of a catalyst by estimating a heat generation amount of combustible substances in a catalyst casing or by estimating a heat generation amount per unit flow amount of the combustible substances supplied to the catalyst.

Furthermore, the present invention has an object to provide a catalyst deterioration detecting apparatus which is capable of performing a highly accurate detection of catalyst deteriorated condition which is not adversely influenced by measuring error of the exhaust gas temperature.

In order to accomplish the above and other related objects, the present invention provides a first catalyst deterioration detecting apparatus for detecting a deteriorated condition of a catalyst placed in a catalyst casing incorporated in an exhaust gas purification system which purifies harmful substances contained in exhaust gas of an engine. The first catalyst deterioration detecting apparatus comprises an upstream exhaust gas temperature sensor for measuring an upstream exhaust gas temperature representing a temperature of exhaust gas residing at an upstream side of the catalyst, and a downstream exhaust gas temperature sensor for measuring a downstream exhaust gas temperature representing a temperature of exhaust gas residing at a downstream side of the catalyst. An engine information detecting means is provided for detecting supplemental engine information other than temperature information obtained from the upstream exhaust gas temperature sensor and the downstream exhaust gas temperature sensor. And, a catalyst deterioration judging means is provided for estimating a heat generation amount per unit flow amount of the combustible substances supplied to the catalyst based on based on the temperature information and the supplemental engine information when the combustible substances react with the catalyst in the catalyst casing. The catalyst deterioration judging means makes a decision that the catalyst is deteriorated when the estimated heat generation amount per unit flow amount of the combustible substances is smaller than a predetermined judging value. The heat generation amount per unit flow amount of the combustible substances is obtained by multiplying a catalytic purification rate and the heat generation amount of the combustible substances.

With this arrangement, it becomes possible to accurately detect the deteriorated condition of the catalyst placed in the catalyst casing incorporated in the exhaust gas purification system. The present invention provides a high-accurate and non-expensive catalyst deterioration detecting apparatus.

With this arrangement, the catalytic purification rate can be accurately obtained by accurately controlling the concentration of the combustible substances and estimating a heat generation amount per unit flow amount of the combustible substances. For example, this makes it possible to accurately discriminate high purification plots from low purification plots with respect to a reference catalytic purification rate (e.g., 50%) line.

The present invention provides a second catalyst deterioration detecting apparatus for detecting a deteriorated condition of a catalyst placed in a catalyst casing incorporated in an exhaust gas purification system which purifies harmful substances contained in exhaust gas of an engine. The second catalyst deterioration detecting apparatus comprises an upstream exhaust gas temperature sensor for measuring an upstream exhaust gas temperature representing a temperature of exhaust gas residing at an upstream side of the catalyst and a downstream exhaust gas temperature sensor for measuring a downstream exhaust gas temperature representing a temperature of exhaust gas residing at a downstream side of the catalyst. An engine information detecting means is provided for detecting supplemental engine information other than temperature information obtained from the upstream exhaust gas temperature sensor and the downstream exhaust gas temperature sensor. An operation mode switching means is provided for switching an engine operating condition between a first operation mode and a second operation mode which are discriminable in an emission amount of the combustible substances contained in the exhaust gas of the engine. And, a catalyst deterioration judging means is provided for estimating a first heat generation amount per unit flow amount of the combustible substances supplied to the catalyst during the first operation mode and also a second heat generation amount per unit flow amount of the combustible substances supplied to the catalyst during the second operation mode based on the temperature information and the supplemental engine information. The catalyst deterioration judging means makes a decision that the catalyst is deteriorated when an estimated difference between the first heat generation amount and the second heat generation amount is smaller than a predetermined judging value (D').

With this arrangement, it becomes possible to accurately detect the deteriorated condition of the catalyst held in the catalyst casing incorporated in the exhaust gas purification system. According to the second catalyst deterioration detecting apparatus, when the same type exhaust gas temperature sensors are used to measure the upstream and downstream exhaust gas temperatures, the measuring errors inherent to these sensors can be automatically canceled through a subtraction for obtaining the difference between the upstream and downstream exhaust gas temperatures. Hence, it becomes possible to realize high-accurate catalyst deterioration judgement not substantially influenced by the measuring errors of the adopted exhaust gas temperature sensors.

According to the catalyst deterioration detecting apparatus of the present invention, it is preferable that the supplemental engine information is an atmospheric temperature or an ambient temperature. The heat generation amount per unit flow amount of the combustible substances supplied to the catalyst is determined considering a heat transfer model of an exhaust gas purification system including a catalyst casing. From this heat transfer model, a first function expression with a variable representing a temperature difference between the upstream exhaust gas temperature and the downstream exhaust gas temperature is introduced.

Furthermore, from this heat transfer model, a second function expression with a variable representing temperature difference between the upstream or downstream exhaust gas temperature and the atmospheric or ambient temperature is introduced.

With this arrangement, it becomes possible to accurately estimate the heat generation amount per unit flow amount of the combustible substances in the catalyst casing of the exhaust gas purification system. When the estimated heat generation amount per unit flow amount of the combustible substances is smaller than the predetermined judging value, the deteriorated condition of the catalyst is confirmed.

According to the catalyst deterioration detecting apparatus of the present invention, it is preferable that the estimation of the heat generation amount per unit flow amount of the combustible substances includes a correcting process for correcting an estimated heat generation amount based on an intake air flow amount or an exhaust gas flow amount as well as based on a traveling speed of a vehicle mounting the exhaust gas purification system.

Furthermore, it is preferable that the estimation of the heat generation amount per unit flow amount of the combustible substances is performed during a stationary or quasi-stationary operating condition of the engine.

Furthermore, the heat generation amount per unit flow amount of the combustible substances can be obtained by multiplying a catalytic purification rate and the heat generation amount of the combustible substances.

Furthermore, it is preferable that the upstream exhaust gas temperature sensor or the downstream exhaust gas temperature sensor is made of a thermistor or a metal resistor whose evaluation function error is within a range of ±15%, the evaluation function error being caused by the upstream exhaust gas temperature or the downstream exhaust gas temperature.

With this arrangement, it becomes possible to suppress the evaluation function error to ±21% or less. It becomes possible to give a decision that the catalyst having a catalytic purification rate of 80% can be judged as being normal (namely, as having a purification rate larger than 50%) when the flow amount of the combustible substances (HC) per unit time is 50 g/hr.

Furthermore, it is preferable that the engine is a direct-injection type diesel engine which selectively performs a post fuel injection in addition to a main fuel injection. The posit fuel injection follows the main fuel injection by a delayed timing of a predetermined crank angle. In this case, the concentration of the combustible substances contained in exhaust gas of the direct-injection type diesel engine varies in response to a switching between a first operating condition where both of the main fuel injection and the post fuel injection are performed and a second operating condition where only the main fuel injection is performed.

It is also preferable that the catalyst is an oxidizing catalyst or a ternary catalyst which oxidizes hydrocarbon (HC) contained as one of the harmful substances in the exhaust gas of the direct-injection type diesel engine. And, the catalyst of the catalyst casing is held on a surface of a diesel particulate filter which traps particulates emitted from the direct-injection type diesel engine.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENT

Figure 1:
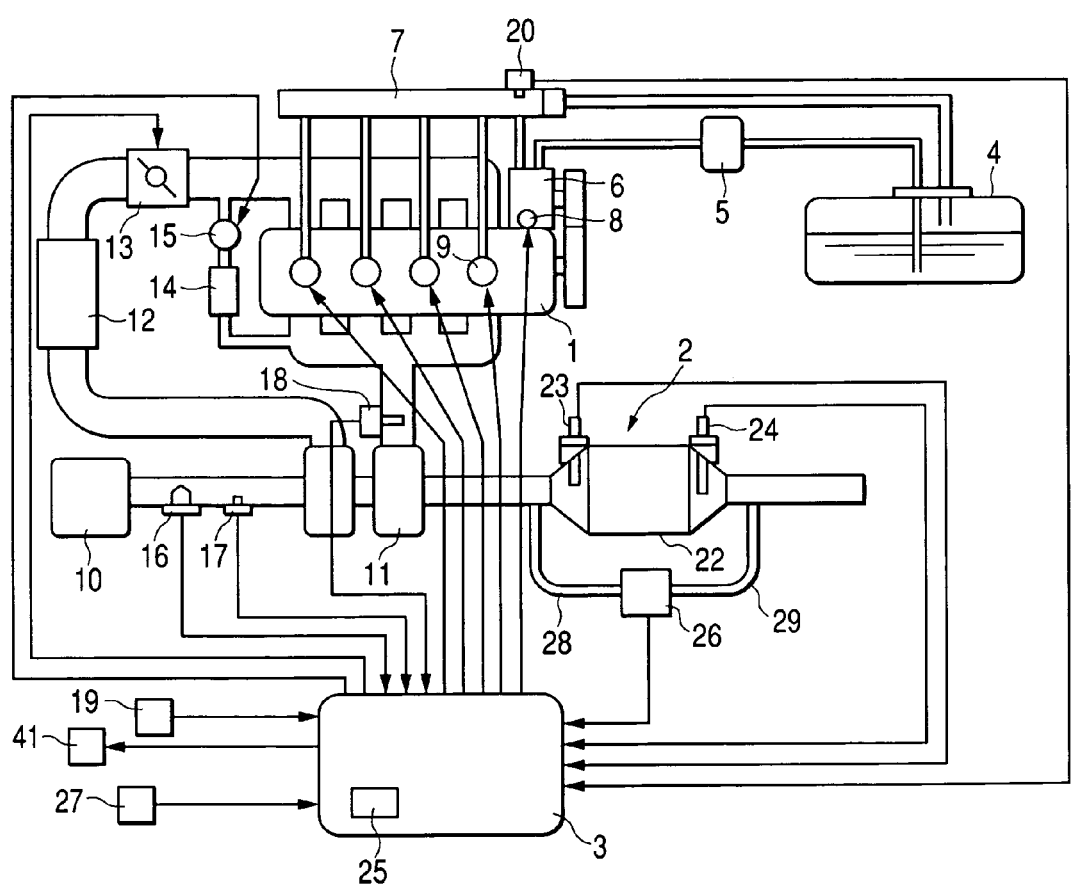
FIG. 1 is a schematic view showing an overall arrangement of a diesel engine control system in accordance with a preferred embodiment of the present invention.

A preferred embodiment of the present invention will be explained hereinafter with reference to attached drawings. Identical parts are denoted by the same reference numerals throughout the drawings.

FIG. 1 shows an overall arrangement of a diesel engine control system. The diesel engine control system in according to this embodiment comprises a diesel engine 1 for an automotive vehicle. A common-rail type fuel injection apparatus is provided for injecting fuel into a combustion chamber of each cylinder of engine 1. A catalytic converter 2, serving as exhaust gas purification system for a diesel engine, is equipped in an exhaust gas passage of the engine 1. The catalytic converter 2 oxidizes harmful substances contained in the exhaust gas into harmless substances. For example, catalytic converter 2 converts carbon monoxide (CO) and hydrocarbon (HC) into carbon dioxide ($CO_2$) and water vapor ($H_2O$), respectively.

A catalyst deterioration detecting apparatus, associated with engine 1, detects deterioration of a catalyst which oxidizes combustible substances (such as HC) contained in the exhaust gas of engine 1. A catalyst deterioration alarming apparatus, also associated with engine 1, generates an alarm by using an alarm lamp 41 when any deteriorated condition of the catalyst is detected by the catalyst deterioration detecting apparatus.

The engine 1 is a direct-injection type diesel engine which injects high-pressure fuel into a single combustion chamber defined between a cylinder head and the top of a piston reciprocating in the cylinder. The injected fuel is atomized and mixed with a swirl of intake air and forms a stratified gas mixture in the combustion chamber.

The common-rail fuel injection apparatus includes various sensors which detect the operating condition of engine 1, the traveling condition of an automotive vehicle, and operating conditions of a driver. The common-rail fuel injection apparatus includes an electronic control unit (ECU) 3 which calculates an optimum fuel injection amount and an optimum fuel injection timing based on the data obtained from the sensors. The common-rail fuel injection apparatus includes actuators which actuate electromagnetic fuel injectors 9 in response to control signals supplied from ECU 3.

The common-rail fuel injection apparatus includes a fuel piping arrangement equipped with a fuel injection pump (i.e., pressurized fuel feed pump) 6. The fuel injection pump 6 has a built-in feed pump which sucks up fuel via a fuel filter 5 from a fuel tank 4 mounted on a vehicle body. The fuel injection pump 6 pressurizes the sucked-up fuel and outputs high-pressure fuel from its outlet port. A common rail 7, serving as accumulator provided in the fuel piping arrangement, stores the high-pressure fuel supplied from the fuel injection pump 6.

The fuel injection pump 6 is equipped with an electromagnetic valve 8 which adjusts a feed amount of high-pressure fuel supplied to the common rail 7 via the fuel piping in accordance with a control signal supplied from ECU 3. Thus, the fuel injection pump 6 changes a fuel injection pressure (i.e., common rail pressure) in accordance with the control signal supplied from ECU 3.

The fuel stored in the fuel tank 4, when sucked by the fuel injection pump 6, passes the fuel filter 5 and enters into the fuel injection pump 6. The common rail 7 is equipped with a fuel pressure sensor 20 to detect the fuel pressure of the fuel stored in the common rail 7. ECU 3 controls the electromagnetic valve 8 of the fuel injection pump 6 so as to optimize the fuel pressure in the common rail 7 in accordance with the operating conditions of the engine 1.

Furthermore, the high-pressure fuel flows in the fuel pipe and reaches respective fuel injectors 9 attached to the engine body. Each fuel injector 9 is located above the combustion chamber of a corresponding cylinder. Each injector 9, connected to the common rail 7 via the fuel pipe, injects a predetermined amount of fuel into the corresponding combustion chamber in accordance with a command signal sent from ECU 3. ECU 3 calculates the command (i.e., a fuel injection amount qf and a fuel injection timing θ) optimized based on a required engine torque T, an engine speed Ne. The required engine torque T is obtained from an accelerator opening signal ACCP of an accelerator opening sensor 19. ECU 3 outputs the thus calculated command signal to the injector 9 of each cylinder to realize the optimum combustion of fuel in each combustion chamber.

Figure 2A:
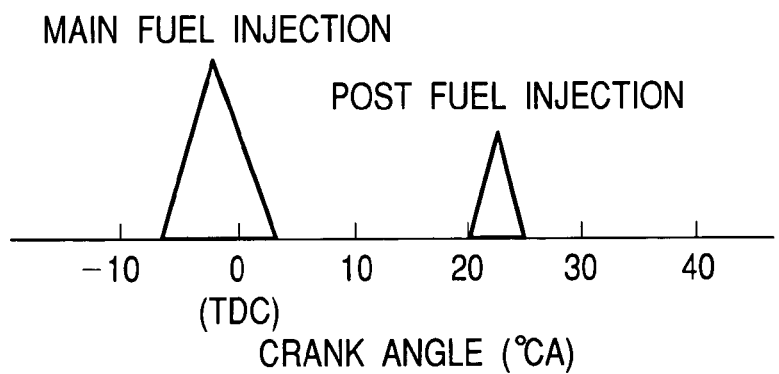
FIG. 2A is a view showing the relationship between a main fuel injection and a post fuel injection with respect to a crank angle.

The fuel injecting operation performed for the diesel engine 1 is chiefly classified into a main fuel injection and a post fuel injection. The main fuel injection is performed at a timing closer to the top dead center (TDC) for generating a required engine power. The post fuel injection is selectively performed in addition to the main fuel injection at a later timing compared with TDC as shown in FIG. 2A. The purpose of performing the post fuel injection is to increase the temperature of exhaust gas and also to send HC (i.e., combustible substances) to a later-described diesel particulate filter (DPF). The HC sent to the DPF reacts with the catalyst held on the surface of this DPF. The temperature of exhaust gas increases. Later-described particulates (PM) abruptly oxidize and burn, and the DPF is refreshed.

For example, the post fuel injection is performed at the crank angle of 20°~50° after TDC. The combustion of fuel injected at the post fuel injection timing is unstable because the post injected fuel burns during the expansion stroke of the engine. Unstable combustion of the post injected fuel increases emission of HC. By utilizing this phenomenon, it is possible to set the concentration of HC (combustible substances) contained in exhaust gas to a higher level compared with that in an ordinary engine operation mode wherein only the main fuel injection is performed.

Returning to FIG. 1, the air is introduced into an intake passage of the engine 1 via an air cleaner 10. A turbocharger 11, provided downstream of the air cleaner 10 in the intake passage, pressures the intake air. An intercooler 12, provided downstream of the turbocharger 11 in the intake passage, cools the intake air. A throttle valve 13, provided downstream of the intaercooler 12 in the intake passage, adjusts an air intake amount introduced into the cylinders of engine 1.

The intake air is mixed with the atomized fuel in the combustion chamber of each cylinder of engine 1. The gas mixture is compressed by the piston and ignited to burn in the combustion chambers. After finishing the combustion of fuel, the exhaust gas engine 1 discharges the exhaust gas from the combustion chambers into an exhaust passage. The flow of exhaust gas rotates the turbine of turbocharger 11 interposed in the exhaust passage. Thus, the intake air flowing in the intake passage is compressed by the turbocharger 11 driven by the flow of exhaust gas. The exhaust gas passes through the catalytic converter 2 accommodating a particulate filter (DPF) 21 therein and goes out of the exhaust passage into the air.

The diesel engine control system of this embodiment comprises an exhaust gas recirculating apparatus which recirculates part of the exhaust gas into the intake passage via an EGR cooler 14 and an EGR valve 15. The purpose of recirculating the exhaust gas partly into the intake passage is to moderate the combustion of fuel in the combustion chambers and as a result to reduce the emission of harmful substances, such as NOx, generated through the combustion of fuel. The EGR cooler 14 reduces the temperature of the exhaust gas flowing in the recirculating passage to increase the charging efficiency of recirculated exhaust gas. The EGR valve 15 and the throttle valve 13 cooperatively control an exhaust gas recirculating amount in accordance with control signals supplied from ECU 3. ECU 3 calculates an optimum EGR amount based on various engine information. The exhaust gas recirculating amount is thus optimized in accordance with engine operating conditions.

An oxygen concentration sensor 18, installed in the exhaust passage, detects the concentration of oxygen in the exhaust gas. EGR valve 15 is also controlled to perform a fine adjustment of oxygen concentration. ECU 3 feedback controls the opening of EGR valve 15 based on the signal of oxygen concentration sensor 18 so as to adjust the oxygen concentration ($\lambda$) to a target value.

Figure 2B:
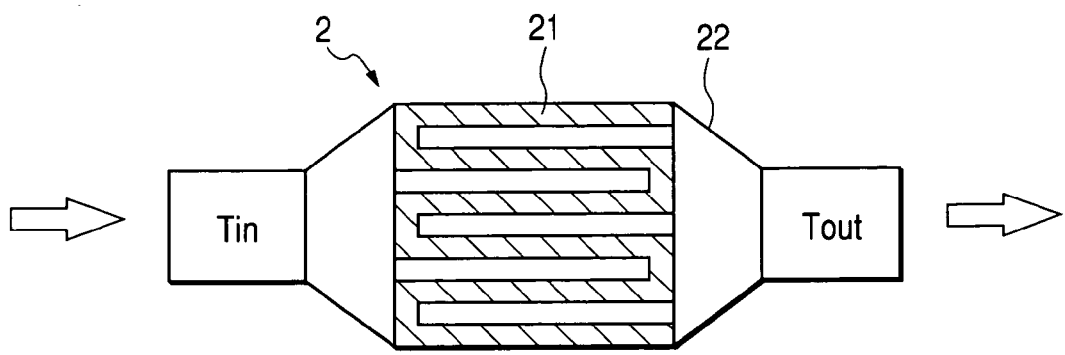
FIG. 2B is a schematic view showing a detailed arrangement of a catalytic converter in accordance with the preferred embodiment of the present invention.

Next, the catalytic converter 2 of this embodiment will be explained with reference to FIGS. 1 and 2. FIG. 2B shows a detailed arrangement of catalytic converter 2.

The catalytic converter 2 comprises DPF 21 held in a metallic catalyst casing 22. DPF 21 constitutes a complicated exhaust passage. The catalyst held on the surface of DPF 21. DPF 21 traps the particulates (hereinafter referred to as PM) emitted from the engine 1 which include carbon soot, unburnt fuel, oil and other polymetric hydrocarbon (HC). DPF 21 is a wall flow type which is constituted by porous ceramics and has the catalyst coated on the DPF surface. DPF 21 can be also constituted by other ceramic group filters, such as a honeycomb filter, a form filter, a fiver filter etc. Alternatively, DPF 21 can be constituted by a metallic filter.

The catalyst casing 22 consists of an upstream side truncated cone portion in which a later-described first exhaust gas temperature sensor 23 is installed, a cylindrical container portion in which DPF 21 is accommodated, and a downstream side truncated cone portion in which a later-described second exhaust gas temperature sensor 24 is installed. The exhaust gas flows in the direction shown by the arrow. An upstream/downstream pressure difference sensor 26 is connected via pipes 28 and 29 to pressure detecting holes of the exhaust passage provided at upstream and downstream sides of DPF 21. The upstream/downstream pressure difference sensor 26 receives an upstream pressure Pu and a downstream pressure Pd and generates a pressure difference signal representing the difference between Pu and Pd. The pressure difference signal is sent to ECU 3.

The first exhaust gas temperature sensor 23 is located at an immediate upstream side of DPF 21 to measure the upstream exhaust gas temperature. The second exhaust gas temperature sensor 24 is located at an immediate downstream side of DPF 21 to measure the downstream exhaust gas temperature. The first exhaust gas temperature sensor 23 and the second exhaust gas temperature sensor 24 send an upstream exhaust gas temperature signal and a downstream exhaust gas temperature signal to ECU 3.

Each of the first exhaust gas temperature sensor 23 and the second exhaust gas temperature sensor 24 is constituted by a protecting pipe attached to the catalyst casing 22 of catalytic converter 2, a thermistor or a Pt or comparable metal resistor placed at the distal end of this a protecting pipe, and a signal line outputting a signal from the thermistor or the Pt or comparable metal resistor.

ECU 3, serving as engine information detecting means of the present invention, has a microcomputer which consists of a control and calculation processor (CPU), program and data memories (RAM, ROM), timers, and I/O ports. An airflow meter 16, provided at the downstream side of the air cleaner 10, detects a flow amount of intake air. An intake temperature sensor 17, provided at the downstream side of the air cleaner 10, detects a temperature of intake air. An engine speed sensor, e.g., an electromagnetic pickup sensor provided in the vicinity of a crank shaft of engine 1, detects a rotational speed Ne of engine 1. An intake pressure sensor, provided in the intake passage, detects a pressure of intake air.

ECU 3 is connected to the airflow meter 16, the intake temperature sensor 17, the oxygen concentration sensor 18, the accelerator opening sensor 19, the engine speed sensor, the intake pressure sensor, the first exhaust gas temperature sensor 23 and the second exhaust gas temperature sensor 24. Analog output signals of these sensors are converted into digital signals through A/D converters before they are sent to ECU 3. ECU 3 input various engine operation data through these sensors. ECU 3 is connected to the upstream/downstream pressure difference sensor 26. An analog output signal of upstream/downstream pressure difference sensor 26 is converted into a digital signal and sent to ECU 3.

Furthermore, ECU 3 constitutes a catalyst deterioration detecting apparatus for detecting a deteriorated condition of the catalyst held on DPF 21 of catalytic converter 2 of engine 1. Especially, the catalyst of this embodiment oxidizes the combustible substances (e.g., HC) contained in exhaust gas of engine 1. ECU 3 constitutes a catalyst deterioration alarming apparatus for generating an alarm by using an alarm lamp 41 when deterioration of the catalyst is detected.

Furthermore, ECU 3 constitutes an operation mode switching means for switching the engine operating condition between a first operation mode and a second operation mode which are discriminable from each other in the emission amount (i.e., the concentration) of the combustible substances (e.g., HC) contained in the exhaust gas of engine 1. During the first operation mode, the post fuel injection is performed in addition to the main fuel injection. During the second operation mode, only the main fuel injection is performed. The emission amount, i.e., the concentration, of the combustible substances (e.g., HC) is set to a higher value in the second operation mode compared with that in the first operation mode.

Other than the temperature information obtained from the first exhaust gas temperature sensor 23 and the second exhaust gas temperature sensor 24, the engine information is obtained from the airflow meter 16, the intake temperature sensor 17, the oxygen concentration sensor 18, the accelerator sensor 19, the engine speed sensor, the intake pressure sensor, or the like.

ECU 3 is equipped with an air temperature sensor 25 which detects an atmospheric temperature (i.e., an ambient temperature). ECU 3 is connected to a vehicle speed sensor 27 which detects a traveling speed Vs of a vehicle mounting this engine. ECU 3 turns on the alarm lamp 41 to inform serious trouble or failure of the control system of a driver or any other passenger in the vehicle.

Figure 3:
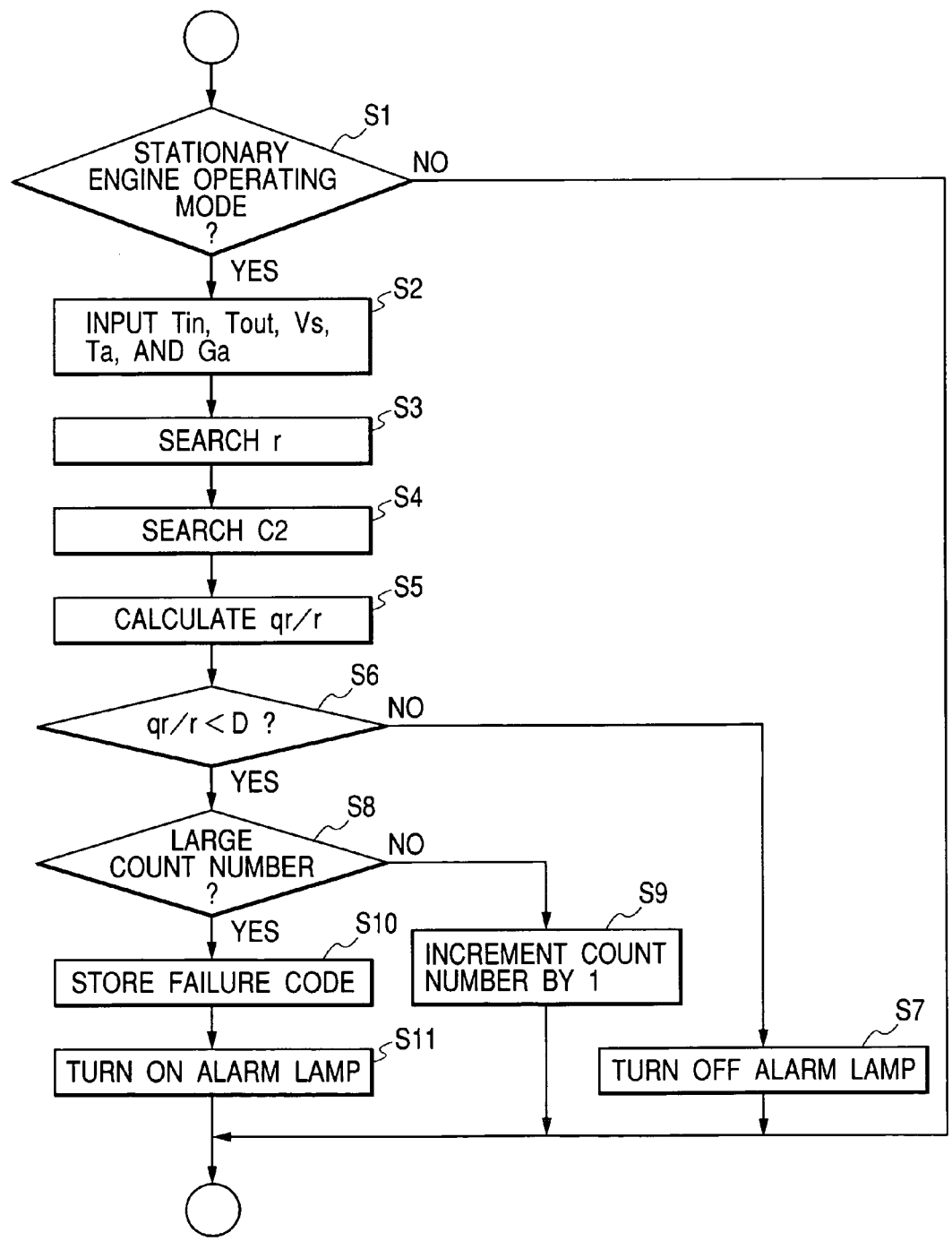
FIG. 3 is a flowchart showing the procedure performed in an engine control unit to realize a catalyst deterioration detecting method in accordance with the preferred embodiment of the present invention.

FIG. 3 is a flowchart showing the procedure performed in ECU 3 to realize a catalyst deterioration detecting method (first control method) in accordance with the preferred embodiment of the present invention. The processing shown in this flowchart is executed at every computation timing of the microcomputer.

First, in step S1, ECU 3 checks whether or not the engine 1 is in a stationary or quasi-stationary operating condition. When the judgement result is NO, this control routine ends and returns to a main routine performed for the fuel injection and the ignition timing control of the engine 1.

When the judgement result is YES in step S1, namely when the engine 1 is in the stationary or quasi-stationary operating condition, it is judged that the engine 1 is presently driven at substantially the same engine speed with substantially the same fuel injection amount.

Next, in step S2, ECU 3 inputs the upstream exhaust gas temperature Tin, the downstream exhaust gas temperature Tout, the vehicle speed Vs, the air temperature Ta, and the intake airflow amount Ga.

Figure 4:
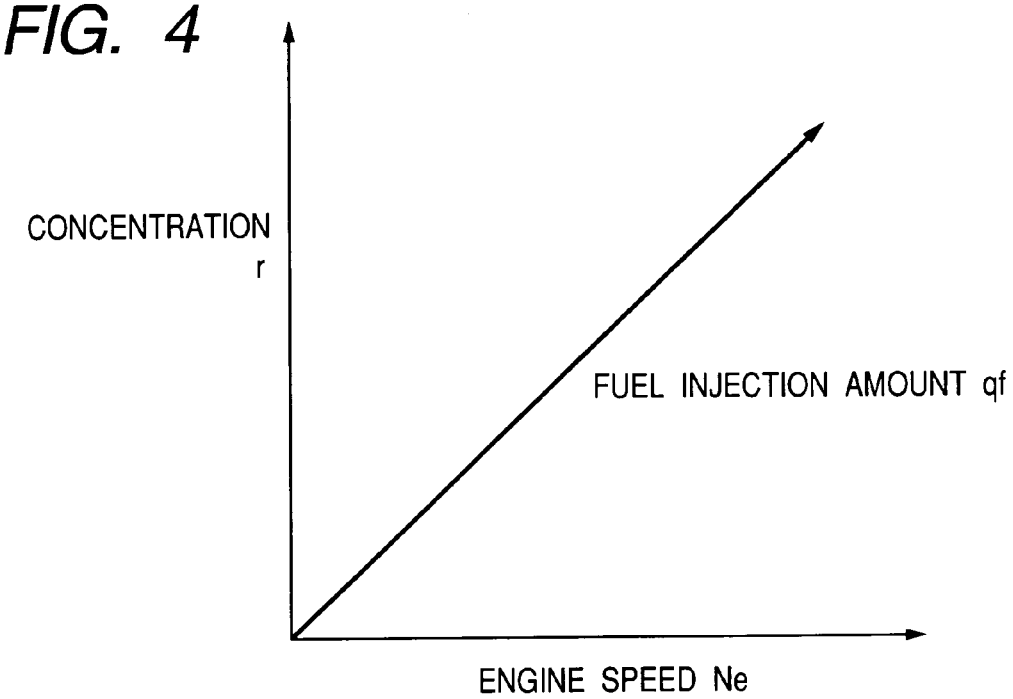
FIG. 4 is a graph showing a relationship among HC concentration, engine speed Ne, and fuel injection amount in accordance with the preferred embodiment of the present invention.

Next, in step S3, ECU 3 searches concentration 'r' of combustible substances (i.e., HC) contained in exhaust gas of engine 1 with reference to a map shown in FIG. 4. The map shown in FIG. 4 defines the relationship between concentration 'r' and engine speed Ne in relation to a fuel ignition amount qf.

Figure 5:
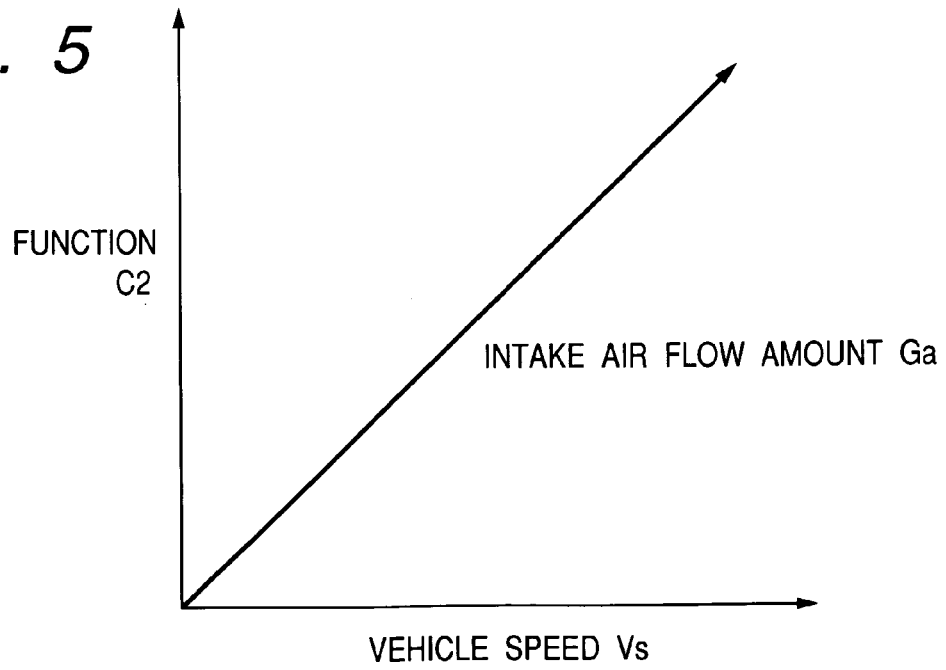
FIG. 5 is a graph showing a relationship among function C2, vehicle speed Vs, and intake air flow amount in accordance with the preferred embodiment of the present invention.

Next, in step S4, ECU 3 searches a value of function C2 with reference to a map shown in FIG. 5. Then, in step S5, ECU 3 calculates a heat generation amount qr/r per unit flow amount of the combustible substances. Then, in step S6, ECU 3 checks whether or not the calculated heat generation amount qr/r is smaller than a predetermined judgement value D. When the judgement result is NO (i.e., qr/r≧D) in step S6, ECU 3 turns off the alarm lamp 41 (step S7). Then, this control routine ends and returns to the main routine.

When the judgement result is YES (i.e., qr/r<D) in step S6, ECU 3 checks whether or not a count number representing the total number of acknowledgment (i.e., frequency of YES decision) exceeds a predetermined value (step S8). When the judgement result is NO in step S8, the count number (i.e., the total number of acknowledgment) is incremented by 1 (step S9). Then, this control routine ends and returns to the main routine. When the judgement result is YES in step S8, namely when the count number exceeds the predetermined value, ECU 3 stores a failure code indicating the deterioration of catalyst in the memory (step S10). Then, ECU 3 turns on the alarm lamp 41 (step S11). Then, this control routine ends and returns to the main routine.

As described above, the above-described first control method detects the deteriorated condition of the catalyst held on the DPF 21 in the catalyst casing 22 of catalytic converter 2. Then, the first control method generates an alarm in response to detection of deteriorated condition of the catalyst which oxidizes the combustible substances (HC). In such an onboard diagnosis technique, the first control method introduces a heat transfer model of an exhaust gas purification system including a catalyst oxidizing hydrocarbon contained in the exhaust gas of engine 1. The heat transfer model will be explained later in detail with reference to FIG. 9. The first control method accurately estimates a heat generation amount of the catalyst by using a function expression derived from this heat transfer model. More specifically, the first control method accurately estimates the heat generation amount qr/r per unit flow amount of the combustible substances (HC) in the catalyst casing 22 based on the upstream and downstream exhaust temperatures of the catalyst as well as based on other engine information.

Then, it is judged whether or not the estimated heat generation amount qr/r per unit flow amount of the combustible substances is smaller than the judgement value D. Furthermore, the count number representing the total number of acknowledgment (i.e., frequency of YES decision) is compared with a given value. When the count number exceeds the given value, the catalyst is judged as having been deteriorated. The failure code indicating the deterioration of catalyst is stored in the memory. Meanwhile, the alarm lamp 41 is turned on to inform the deterioration of catalyst of a driver or any other passenger in the vehicle. Accordingly, the first control method of the present invention realizes an accurate and practical detection of catalyst deteriorated condition which is preferably applied to a direct-injection type diesel engine.

Figure 6:
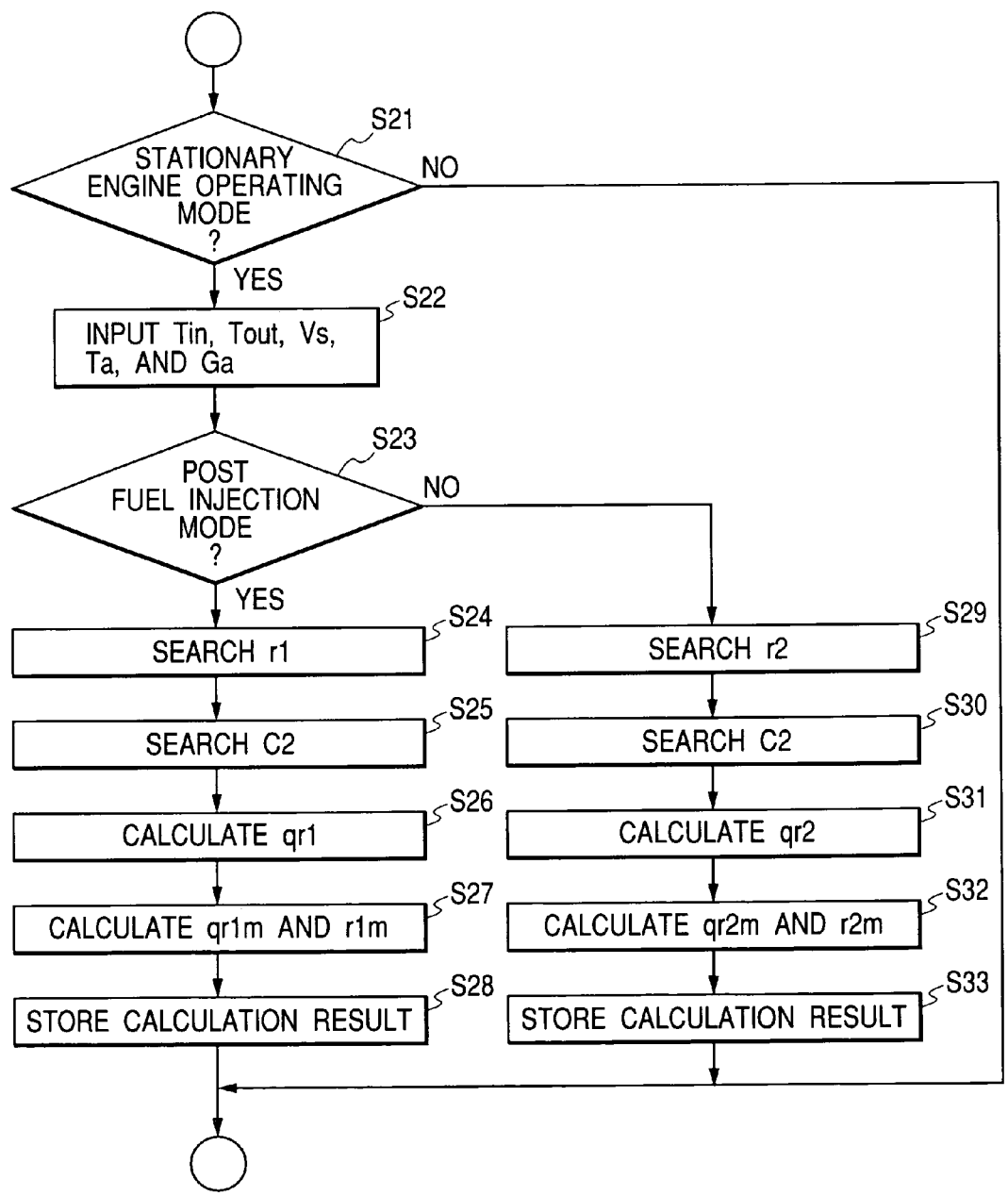
FIGS. 6 and 7 are flowcharts showing the procedure performed in the engine control unit to realize another catalyst deterioration detecting method in accordance with the preferred embodiment of the present invention.
Figure 7:
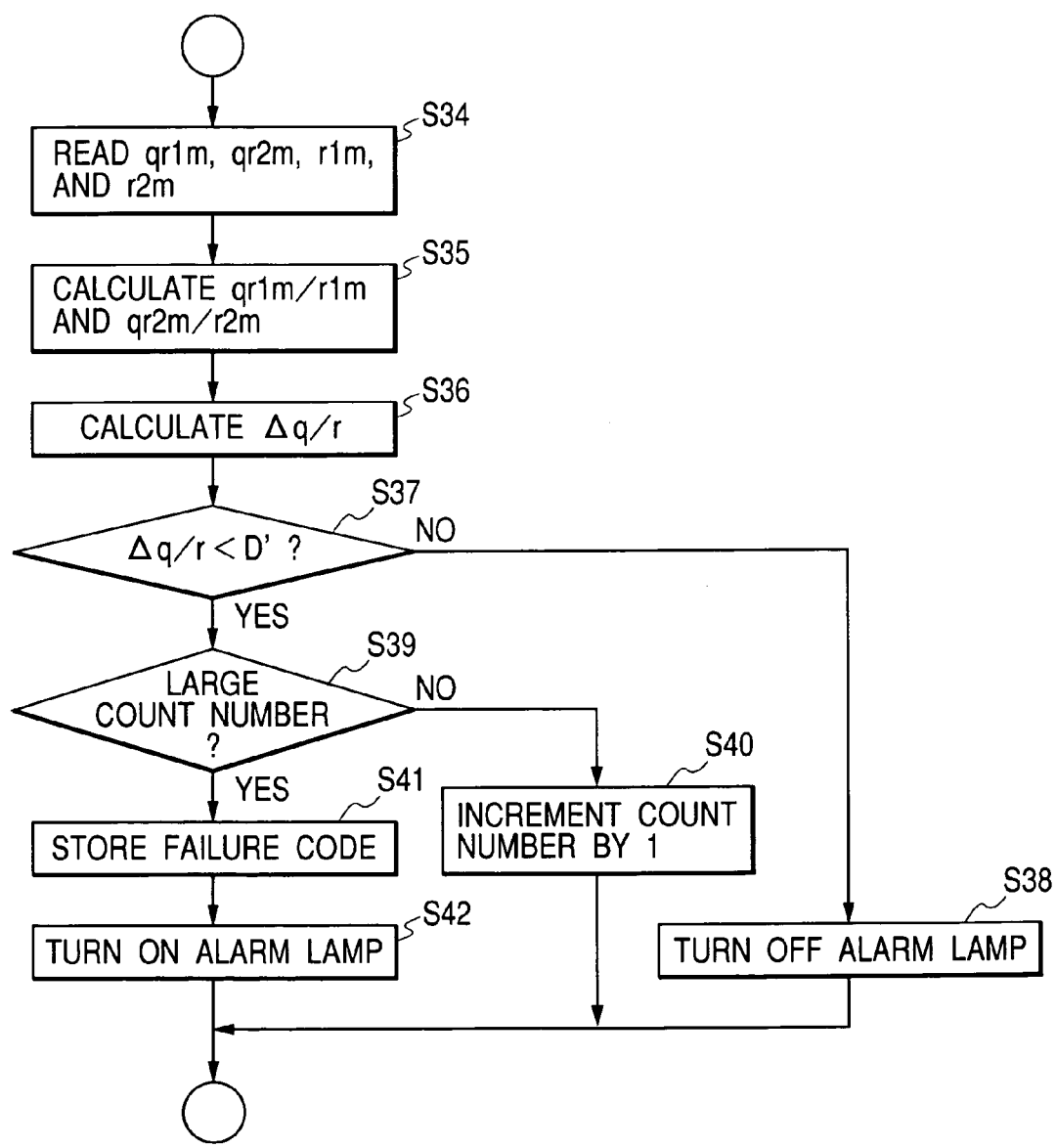

FIGS. 6 and 7 cooperatively show the procedure performed in ECU 3 to realize another catalyst deterioration detecting method (second control method) in accordance with the preferred embodiment of the present invention. The processing shown in this flowchart is executed at every computation timing of the microcomputer. FIG. 6 is a flowchart showing a program for obtaining a concentration of combustible substances contained in exhaust gas and a heat generation amount of combustible substances per unit flow amount of exhaust gas. FIG. 7 is a flowchart showing a program for executing a catalyst deterioration judgement.

First, in step S21, ECU 3 checks whether or not the engine 1 is in a stationary or quasi-stationary operating condition. When the judgement result is NO, this control routine ends and returns to a main routine performed for the fuel injection and the ignition timing control of the engine 1.

When the judgement result is YES in step S21, namely when the engine 1 is in the stationary or quasi-stationary operating condition, it is judged that the engine 1 is presently driven at substantially the same engine speed with substantially the same fuel injection amount.

Next, in step S22, ECU 3 inputs the upstream exhaust gas temperature Tin, the downstream exhaust gas temperature Tout, the vehicle speed Vs, the air temperature Ta, and the intake airflow amount Ga.

Next, in step S23, ECU 3 judges whether or not the engine 1 is in the first operation mode for performing the post fuel injection in addition to the main fuel injection. In other words the first operation mode is performed to increase the concentration of combustible substances (HC).

Figure 8:
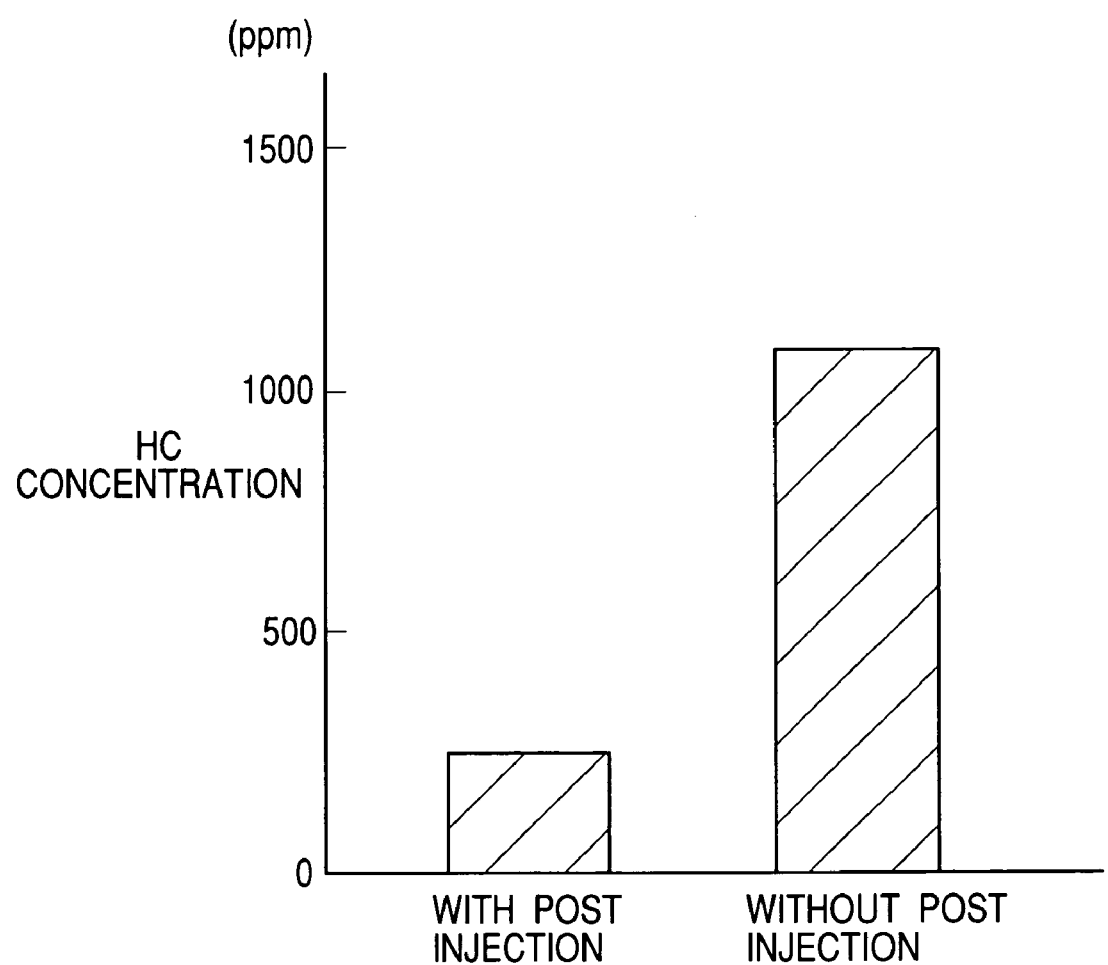
FIG. 8 is a graph showing the change of HC concentration characteristics brought by execution of post fuel injection in accordance with the preferred embodiment of the present invention.

FIG. 8 is a graph showing the change of HC concentration characteristics brought by execution of the post fuel injection. The data of FIG. 8 was obtained through an engine test under the operating conditions that a cylinder volume is 2.0 L, the engine speed is 1,700 rpm, and the engine torque 15 Nm. As understood of FIG. 8, the concentration of combustible substances (HC) during the first operation mode (performing the post fuel injection) is higher than that in the second operation mode (performing no post fuel injection).

When the judgement result is YES in step S23, namely when the post fuel injection is performed, ECU 3 searches the concentration r1 of combustible substances (i.e., HC) contained in exhaust gas of engine 1 with reference to the map shown in FIG. 4 (step S24). Next, in step S25, ECU 3 searches a value of function C2 with reference to the map shown in FIG. 5. Then, in step S26, ECU 3 calculates a heat generation amount qr1 per unit flow amount of exhaust gas. Then, in step S27, ECU 3 obtains mean values of the concentration r1 and the heat generation amount qr1 by respectively obtaining an average of the present value and a previous value by using recurrence relations. Then, in step S28, ECU 3 stores the obtained mean values r1m and qr1m in the memory.

Furthermore, when the judgement result is NO in step S23, namely when no post fuel injection is performed, ECU 3 searches the concentration r2 of combustible substances (i.e., HC) contained in exhaust gas of engine 1 with reference to a map similar to the map shown in FIG. 4 (step S29). Next, in step S30, ECU 3 searches a value of function C2 with reference to the map shown in FIG. 5. Then, in step S31, ECU 3 calculates a heat generation amount qr2 per unit flow amount of exhaust gas. Then, in step S32, ECU 3 obtains mean values of the concentration r2 and the heat generation amount qr2 by respectively obtaining an average of the present value and a previous value by using recurrence relations. Then, in step S33, ECU 3 stores the obtained mean values r2m and qr2m in the memory.

Next, going on the flowchart of FIG. 7, ECU 3 reads qr1m, qr2m, r1m, and r2m (step S34). Then, in step S35, ECU 3 calculates a first heat generation amount $\Delta qr1m/r1m$ per unit flow amount of the combustible substances during the first operation mode (performing the post fuel injection). Furthermore, ECU 3 calculates a second heat generation amount $\Delta qr2m/r2m$ per unit flow amount of the combustible substances during the second operation mode (performing no post fuel injection).

Then, in step S36, ECU 3 calculates a difference between the first heat generation amount $\Delta qr1m/r1m$ and the second heat generation amount $\Delta qr2m/r2m$ to obtain a heat generation amount difference $\Delta q/r$ per unit flow amount of the combustible substances. Then, in step S37, ECU 3 checks whether or not the calculated heat generation amount difference $\Delta q/r$ per unit flow amount of the combustible substances is smaller than a predetermined judgement value D'. When the judgement result is NO (i.e., $\Delta q/r \geq D'$) in step S37, ECU 3 turns off the alarm lamp 41 (step S38). Then, this control routine ends and returns to the main routine.

When the judgement result is YES (i.e., $\Delta q/r<D'$) in step S37, ECU 3 checks whether or not a count number representing the total number of acknowledgment (i.e., frequency of YES decision) exceeds a predetermined value (step S39). When the judgement result is NO in step S39, the count number (i.e., the total number of acknowledgment) is incremented by 1 (step S40). Then, this control routine ends and returns to the main routine. When the judgement result is YES in step S39, namely when the count number exceeds the predetermined value, ECU 3 stores a failure code indicating the deterioration of catalyst in the memory (step S41). Then, ECU 3 turns on the alarm lamp 41 (step S42). Then, this control routine ends and returns to the main routine.

As described above, the above-described second control method inputs the data r1m and qr1m obtained during the first operation mode and the data r2m and qr2m obtained during the second operation mode. The second control method obtains the heat generation amount difference $\Delta q/r$ per unit flow amount of the combustible substances which reflects the influence of executing the post fuel injection.

Then, it is judged whether or not the calculated heat generation amount $\Delta q/r$ per unit flow amount of the combustible substances is smaller than the judgement value D'. Furthermore, the count number representing the total number of acknowledgment (i.e., frequency of YES decision) is compared with a given value. When the count number exceeds the given value, the catalyst is judged as having been deteriorated. The failure code indicating the deterioration of catalyst is stored in the memory. Meanwhile, the alarm lamp 41 is turned on to inform the deterioration of catalyst of a driver or any other passenger in the vehicle.

As described above, the main fuel injection is performed at a timing closer to the top dead center (TDC) for generating a required engine power. On the other hand, the post fuel injection is selectively performed in addition to the main fuel injection at the crank angle of 20°~50° after TDC. The combustion of fuel injected at the post fuel injection timing is unstable because the post injected fuel burns during the expansion stroke of the engine. Unstable combustion of the post injected fuel increases emission of HC. By utilizing this phenomenon, it is possible to set the concentration of HC (combustible substances) contained in exhaust gas to a higher level compared with that in an ordinary engine operation mode wherein only the main fuel injection is performed.

When the engine goes into an engine operating region for judging the deteriorated condition of the catalyst for a predetermined time, the engine alternatively performs the first operation mode performing both of the main and post fuel injections and the second operation mode performing only the main fuel injection. During this operation, the control disclosed in the flowchart of FIGS. 6 and 7 is executed.

As described above, the above-described second control method of the present invention causes the engine to alternately perform two different operation modes (i.e., first and second operation modes) discriminable in the concentration of the combustible substances supplied to the catalyst. The second control method of the present invention estimates the heat generation amount difference $\Delta q/r$ per unit flow amount of the combustible substances which is caused due to execution of the post fuel injection. Like the first control method, the above-described second control method obtains the heat generation amount difference $\Delta q/r$ per unit flow amount of the combustible substances with reference to the heat transfer model shown in FIG. 9.

Then, the total number of acknowledgment is counted in response to each YES decision as to whether or not the calculated heat generation amount difference $\Delta q/r$ per unit flow amount of the combustible substances is smaller than the judgement value D'.

When the count number exceeds the given value, the catalyst is judged as having been deteriorated.

According to the second control method, it becomes possible to cancel the measuring errors inherent to two exhaust gas temperature sensors 23 and 24 through a subtraction for obtaining the heat generation amount difference ($\Delta q/r$) per unit flow amount of the combustible substances between the first and second operation modes discriminable in the concentration of the combustible substances (HC) supplied to the catalyst.

Figure 9:
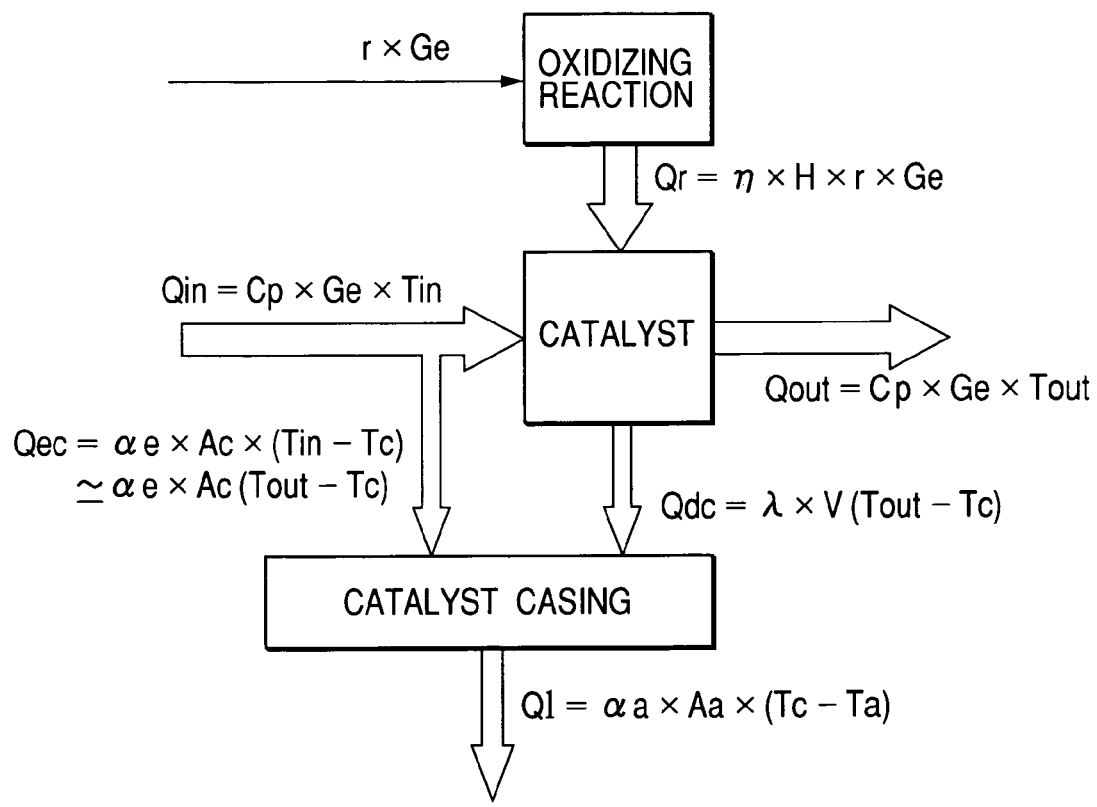
FIG. 9 is a view showing a heat transfer model of the catalytic converter.

FIG. 9 shows the heat transfer model of the catalytic converter 2 used in the above-described first and second control methods. In this heat transfer model, the catalytic converter 2 is related to a total of six heat transfers.

First of all, a combustible substance inflow amount r×Ge is obtained by multiplying the combustible substance (HC) concentration 'r' with an exhaust gas flow amount Ge. The exhaust gas flow amount Ge is proportional with the intake air flow amount Ga.

Next, a heat generation amount Qr caused by the oxidation of combustible substances is obtained by multiplying the catalytic purification rate η, the heat generation amount H of the combustible substances (HC), and the combustible substance inflow amount r×Ge. The heat generation amount Qr is thus expressed by η×H×r×Ge.

Furthermore, an inflow heat amount Qin is obtained by multiplying the specific heat Cp of exhaust gas, the exhaust gas flow amount Ge, and the upstream exhaust gas temperature Tin. The inflow heat amount Qin is thus expressed by Cp×Ge×Tin.

A heat transfer amount Qec, transmitted from exhaust gas to catalyst casing 22, is obtained by multiplying a temperature difference Tin−Tc between the upstream exhaust gas temperature Tin and the catalyst casing temperature Tc, a heat transfer coefficient αe from the exhaust gas to the catalyst casing 22, and a heat radiation area Ae from the exhaust gas to the catalyst casing 22. The heat transfer amount Qec is thus expressed by αe×Ae×(Tin−Tc).

Meanwhile, the heat transfer amount Qec can be obtained by multiplying a difference Tout−Tc between the downstream exhaust gas temperature Tout and the catalyst casing temperature Tc, the heat transfer coefficient αe from the exhaust gas to the catalyst casing 22, and the heat radiation area Ae from the exhaust gas to the catalyst casing 22. The heat transfer amount Qec is thus expressed by αe×Ae×(Tout−Tc).

An outflow heat amount Qout is obtained by multiplying the specific heat Cp of exhaust gas, the exhaust gas flow amount Ge, and the downstream exhaust gas temperature Tout. The outflow heat amount Qout is thus expressed by Cp×Ge×Tout.

Furthermore, a heat transfer amount Qdc, transmitted from catalyst to catalyst casing 22, is obtained by multiplying a temperature difference Tout−Tc between the downstream exhaust gas temperature Tout and the catalyst casing temperature Tc, a heat conductivity λ, and a heat conductive length×area V. The heat transfer amount Qdc is thus expressed by λ×V×(Tout−Tc).

Furthermore, an atmospheric heat radiation amount Q1 is obtained by multiplying a temperature difference Tc−Ta between the catalyst casing temperature Tc and the air temperature Ta, a heat transfer coefficient αa from the catalyst casing 22 to the air, and a heat radiation area Aa from the catalyst casing 22 to the air. The atmospheric heat radiation amount Q1 is thus expressed by αa×Aa×(Tc−Ta).

The heat generation amount qr per unit flow amount of the exhaust gas is defined by an equation qr=Qr/Ge.

From the above-described heat transfer model, the heat generation amount qr per unit flow amount of exhaust gas is obtained by multiplying the catalytic purification rate η, the heat generation amount H of combustible substances (HC), and the concentration 'r' of combustible substances (HC). The heat generation amount qr per unit flow amount of the exhaust gas is thus expressed by η×H×r. More specifically, the heat generation amount qr per unit flow amount of exhaust gas is defined by using a function expression {C1×(Tout−Tin)+C2×(Tout−Ta)}.

In this case, the heat generation amount H of combustible substances (HC) is constant. C1 (=Cp representing the specific heat of exhaust gas) is constant. C2 (=αa×Aa×(αe×Ac+λ×V)/(αa×Aa+αe×Ac+λ×V)/Ge) comprises a function (αa) of measurable vehicle speed and an exhaust gas flow amount Ge. C2 can be obtained from the map shown in FIG. 5.

Thus, the catalytic purification rate η can be easily obtained by accurately controlling the concentration 'r' of combustible substances (HC) contained in exhaust gas and measuring the downstream exhaust gas temperature Tout, the upstream exhaust gas temperature Tin, and the air temperature Ta.

Figure 10:
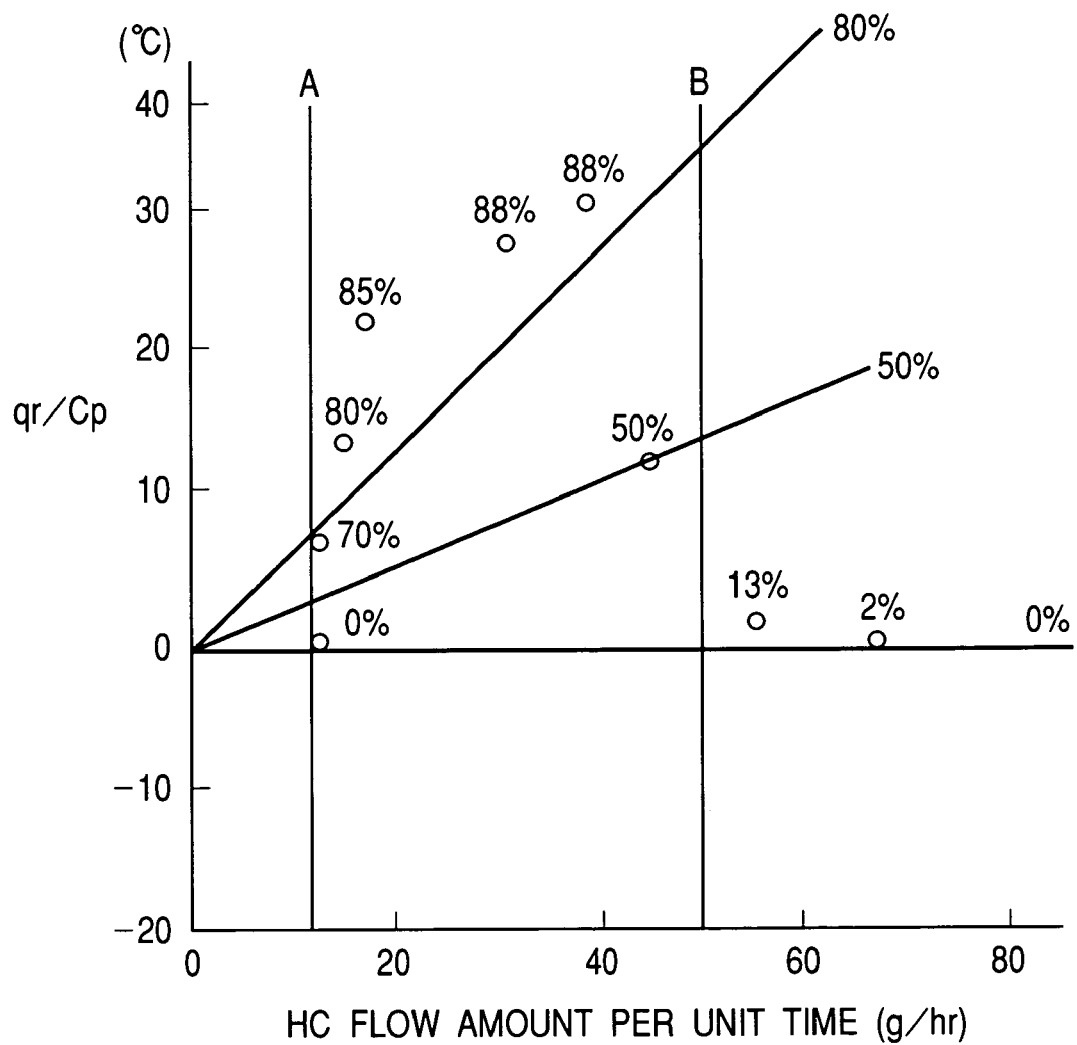
FIG. 10 is a graph showing a relationship among equation function (qr/Cp), HC flow amount per unit time, and catalytic purification rate in accordance with the preferred embodiment of the present invention.
Figure 11:
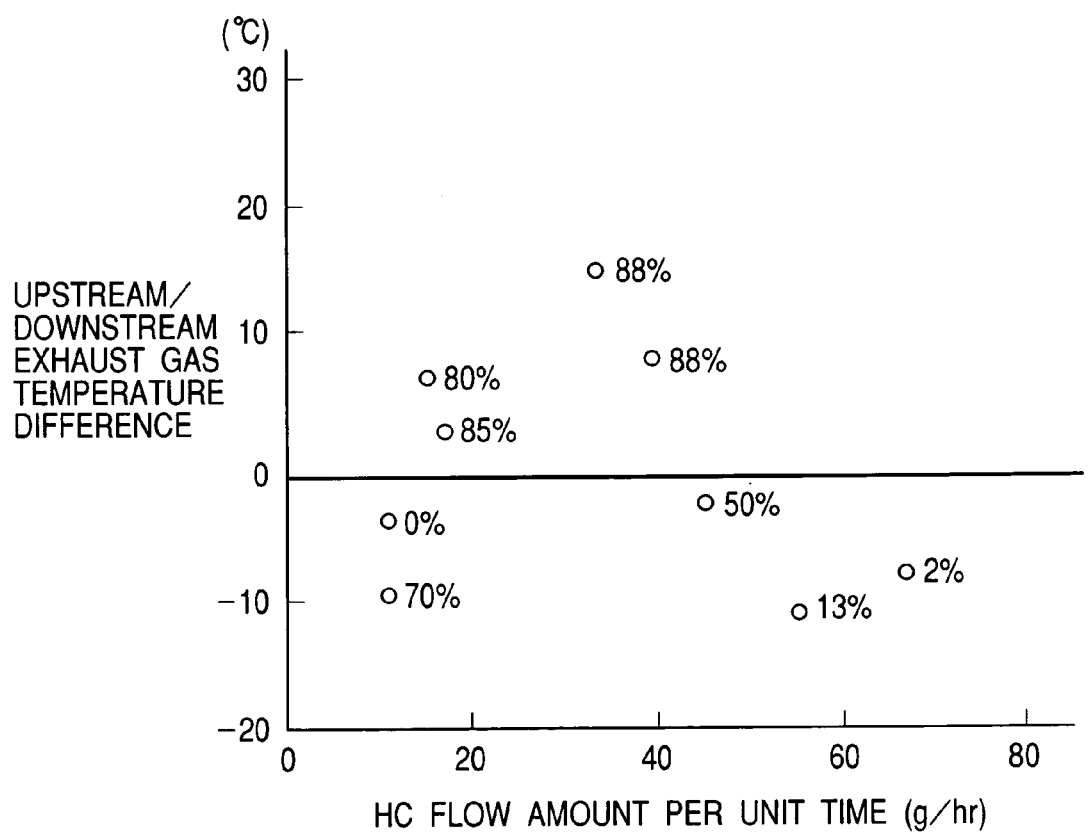
FIG. 11 is a graph showing a conventional relationship among upstream/downstream exhaust gas temperature, HC flow amount per unit time, and catalytic purification rate.

FIG. 10 is a graph showing a relationship among evaluation function qr/Cp, HC flow amount per unit time (g/hr), and catalytic purification rate (%) obtained based on the data similar to those shown in FIG. 11.

As understood from FIG. 10, plots of high purification rates are accurately discriminated from plots of low purification rates with respect to a 50% purification rate line. Thus, it becomes possible to judge the deterioration of a catalyst oxidizing the combustible substances (HC) with reference to the relationship shown in FIG. 10. When the flow amount of the combustible substances (HC) contained in exhaust gas is 50 g/hr, the evaluation function error needs to be suppressed to ±21% or less to assure that the catalyst having a catalytic purification rate of 80% can be judged as being normal (namely, as having a purification rate larger than 50%).

To satisfy this requirement, the measuring accuracies of the upstream exhaust gas temperature Tin and the downstream exhaust gas temperature Tout need to be suppressed to ±15% or less. This is an important requirement for establishing the catalyst deterioration judging method of the present invention, and will be satisfied by a high-accurate exhaust gas sensor which is made of a thermistor or a Pt or comparable metal resistor.

Furthermore, the catalyst deterioration judgement is easily performed by evaluating the gradient of an evaluation function obtained in a region between two points A and B shown in FIG. 10. Thus, ECU 3 can accurately perform the catalyst deterioration detecting method (second control method) of the present invention. In this case, a temperature difference Tout−Tin between the upstream exhaust gas temperature Tin and the downstream exhaust gas temperature Tout is obtained based on a subtraction between two exhaust gas temperatures measured by the same exhaust gas temperature sensors at two points. Accordingly, the measuring errors inherent to these sensors can be automatically canceled through this subtraction processing. Hence, it becomes possible to realize high-accurate catalyst deterioration judgement which is not substantially influenced by the measuring errors of the adopted exhaust gas temperature sensors.

According to the above-described embodiment of the present invention, the catalytic converter 2 is an oxidizing catalytic converter which oxidizes carbon monoxide (CO) and hydrocarbon (HC) into carbon dioxide ($CO_2$) and water vapor ($H_2O$) respectively. However, the present invention can be applied to a ternary catalytic converter which not only oxidizes carbon monoxide (CO) and hydrocarbon (HC) but reduces nitrogen oxides (NOx) into harmless substances such as carbon dioxide ($CO_2$), water vapor ($H_2O$), and nitrogen (N2).

What is claimed is:

1. A catalyst deterioration detecting apparatus for detecting a deteriorated condition of a catalyst placed in a catalyst casing incorporated in an exhaust gas purification system which purifies harmful substances contained in exhaust gas of an engine, said catalyst deterioration detecting apparatus comprising:
    an upstream exhaust gas temperature sensor which measures an upstream exhaust gas temperature representing a temperature of exhaust gas residing at an upstream side of said catalyst;
    a downstream exhaust gas temperature sensor which measures a downstream exhaust gas temperature representing a temperature of exhaust gas residing at a downstream side of said catalyst;
    an engine information detector which detects supplemental engine information other than temperature information obtained from said upstream exhaust gas temperature sensor and said downstream exhaust gas temperature sensor, wherein the supplemental engine information relates to an operation of the engine;
    a first controller which switches an engine operating condition between a first operation mode and a second operation mode which are discriminable from each other in a concentration of the combustible substances contained in the exhaust gas of the engine to operate the engine in the first operation mode and then operate the engine in the second operation mode; and
    a second controller which estimates a first heat generation amount per unit flow amount of combustible substances supplied to said catalyst during said first operation mode and also a second heat generation amount per unit flow amount of combustible substances supplied to said catalyst during said second operation mode based on said upstream and downstream exhaust gas temperatures and said supplemental engine information, and which makes a decision that said catalyst is deteriorated when an estimated difference between said first heat generation amount and said second heat generation amount is smaller than a predetermined judging value,
    wherein said supplemental engine information is an atmospheric or ambient temperature, and
    each of the first and second heat generation amounts per unit flow amount of combustible substances is obtained based on a first function expression with a variable representing a temperature difference between said upstream exhaust gas temperature and said downstream exhaust gas temperature as well as a second function expression with a variable representing a temperature difference between said upstream or downstream exhaust gas temperature and said atmospheric or ambient temperature.

2. The catalyst deterioration detecting apparatus in accordance with claim 1, wherein the estimation of said heat generation amount per unit flow amount of said combustible substances includes a correcting process for correcting an estimated heat generation amount based on an intake air flow amount or an exhaust gas flow amount as well as based on a traveling speed of a vehicle mounting said exhaust gas purification system.

3. The catalyst deterioration detecting apparatus in accordance with claim 1, wherein the second controller performs the estimation of said first heat generation amount per unit flow amount of combustible substances and said second heat generation amount per unit flow amount of combustible substances during a stationary or quasi-stationary operating condition of said engine.

4. The catalyst deterioration detecting apparatus in accordance with claim 1, wherein said heat generation amount per unit flow amount of said combustible substances is obtained by multiplying a catalytic purification rate and the heat generation amount of said combustible substances.

5. The catalyst deterioration detecting apparatus in accordance with claim 1, wherein said upstream exhaust gas temperature sensor or said downstream exhaust gas temperature sensor is made of a thermistor or a metal resistor whose evaluation function error is within a range of ±15%, said evaluation function error being caused by said upstream exhaust gas temperature or said downstream exhaust gas temperature.

6. The catalyst deterioration detecting apparatus in accordance with claim 1, wherein said engine is a direct-injection type diesel engine which selectively performs a post fuel injection in addition to a main fuel injection, said posit injection following said main fuel injection by a delayed timing of a predetermined crank angle, and
    the concentration of said combustible substances contained in exhaust gas of said direct-injection type diesel engine varies in response to a switching between a first operating condition where both of said main fuel injection and said post fuel injection are performed and a second operating condition where only said main fuel injection is performed.

7. The catalyst deterioration detecting apparatus in accordance with claim 6, wherein said catalyst is an oxidizing catalyst or a ternary catalyst which oxidizes hydrocarbon contained as one of said harmful substances in the exhaust gas of said direct-injection type diesel engine, and said catalyst of said catalyst casing is placed on a surface of a diesel particulate filter which traps particulates emitted from said direct-injection type diesel engine.

8. The catalyst deterioration detecting apparatus in accordance with claim 1, wherein the second controller detects a first flow amount of the combustible substances in said first operation mode and a second flow amount of the combustible substances in said second operation mode, calculates a first heat generation amount per unit flow amount of first exhaust gas supplied to said catalyst in said first operation mode based on said upstream and downstream exhaust gas temperatures and said supplemental engine information, calculates a second heat generation amount per unit flow amount of second exhaust gas supplied to said catalyst in said second operation mode based on said upstream and downstream exhaust gas temperatures and said supplemental engine information, calculates the first heat generation amount per unit flow amount of combustible substances from the first heat generation amount per unit flow amount of the first exhaust gas and the first flow amount of the combustible substances in said first operation mode, and calculates the second heat generation amount per unit flow amount of combustible substances from the second heat generation amount per unit flow amount of the second exhaust gas and the second flow amount of the combustible substances in said second operation mode.

9. The catalyst deterioration detecting apparatus in accordance with claim 8, wherein
the first controller alternately switches the engine operating condition to alternately perform the operation of the engine in the first operation mode and the operation of the engine in the second operation mode, and
the second controller calculates a mean value of first heat generation amounts per unit flow amount of exhaust gas calculated every operation of the engine in the first operation mode, calculates a mean value of second heat generation amounts per unit flow amount of exhaust gas calculated every operation of the engine in the second operation mode, calculates a mean value of first flow amounts of the combustible substances detected every operation of the engine in the first operation mode, calculates a mean value of second flow amounts of the combustible substances detected every operation of the engine in the second operation mode, calculates the first heat generation amount per unit flow amount of combustible substances from the mean value of the first heat generation amounts per unit flow amount of the exhaust gas and the mean value of the first flow amounts of the combustible substances, and calculates the second heat generation amount per unit flow amount of combustible substances from the mean value of the second heat generation amounts per unit flow amount of the exhaust gas and the mean value of the second flow amount of the combustible substances.

* * * * *